(12) United States Patent
Fleischer et al.

(10) Patent No.: US 10,048,201 B2
(45) Date of Patent: Aug. 14, 2018

(54) FLUID CHANNELS FOR COMPUTATIONAL IMAGING IN OPTOFLUIDIC MICROSCOPES

(71) Applicants: Jason W. Fleischer, Princeton, NJ (US); Nicolas C. Pegard, Princeton, NJ (US)

(72) Inventors: Jason W. Fleischer, Princeton, NJ (US); Nicolas C. Pegard, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 576 days.

(21) Appl. No.: 14/023,455

(22) Filed: Sep. 10, 2013

(65) Prior Publication Data
US 2014/0071452 A1      Mar. 13, 2014

Related U.S. Application Data

(60) Provisional application No. 61/699,020, filed on Sep. 10, 2012, provisional application No. 61/699,003, filed on Sep. 10, 2012.

(51) Int. Cl.
*G01N 21/00* (2006.01)
*G01N 1/10* (2006.01)
(Continued)

(52) U.S. Cl.
CPC ........... *G01N 21/59* (2013.01); *G01N 15/147* (2013.01); *G01N 15/1434* (2013.01);
(Continued)

(58) Field of Classification Search
CPC .... G01B 9/04; G02B 17/002; G02B 19/0076; G02B 21/16; G02B 27/40; G02B 19/0028;
(Continued)

(56) References Cited

U.S. PATENT DOCUMENTS 9,068,916 B2 *   6/2015   Heng ................... G01N 15/147
2002/0001089 A1 * 1/2002   Price ...................... G02B 21/22
                                                                356/601
(Continued)

OTHER PUBLICATIONS

Heng, et al., "Optofluidic Microscopy—a Method for Implementing a High Resolution Optical Microscope on a Chip," Lab on a Chip, vol. 6, pp. 1274-1776 (2006).
(Continued)

*Primary Examiner* — Sunghee Y Gray
(74) *Attorney, Agent, or Firm* — Meagher Emanuel Laks Goldberg & Liao, LLP

(57) ABSTRACT

A microscope is disclosed, the microscope having a light source defining an optical axis along a Z direction and a detector disposed in X-Y direction, orthogonal to the optical axis, the detector configured to capture images of an object. The microscope includes a fluid channel having an inlet and an outlet configured with a fluid flow to transport the object from the inlet to the outlet. The detector is configured to capture a plurality of images of the object as the object moves from the inlet to the outlet. The plurality of images of the object may have different heights of the sample with respect to the detector as the sample flows through the channel. The channel may be tilted with respect to the optical axis. The detector may be tilted with respect to the optical axis.

21 Claims, 9 Drawing Sheets

(51) Int. Cl.
*H01J 40/14* (2006.01)
*G02B 27/10* (2006.01)
*G02B 27/14* (2006.01)
*G01N 21/59* (2006.01)
*G01N 15/14* (2006.01)
*G02B 21/08* (2006.01)
*G02B 21/36* (2006.01)
*G01N 15/10* (2006.01)
*B01L 3/00* (2006.01)

(52) U.S. Cl.
CPC ....... *G01N 15/1475* (2013.01); *G02B 21/086* (2013.01); *G02B 21/367* (2013.01); *B01L 3/502715* (2013.01); *G01N 2015/1006* (2013.01); *G01N 2015/1445* (2013.01)

(58) Field of Classification Search
CPC .. G02B 21/0076; G02B 5/10; G01N 21/6408; G01N 21/0008; G01N 21/6458; G01N 21/05; G01N 15/1404; G01N 2015/1413; B01F 5/0647; B01F 13/0062; B01L 3/502776
USPC .................. 356/440, 432–436, 338, 246, 39; 250/578.1, 428; 382/152
See application file for complete search history.

(56) References Cited

U.S. PATENT DOCUMENTS

| | | | | |
|---|---|---|---|---|
| 2002/0044346 | A1* | 4/2002 | Nguyen | G02B 21/241 359/368 |
| 2005/0046848 | A1* | 3/2005 | Cromwell | G01N 21/6408 356/417 |
| 2009/0014360 | A1* | 1/2009 | Toner | B01D 21/0087 209/208 |
| 2010/0221769 | A1* | 9/2010 | Lu | G01N 15/147 435/29 |
| 2011/0085219 | A1* | 4/2011 | Yang | G02B 5/32 359/15 |
| 2011/0170105 | A1* | 7/2011 | Cui | G02B 21/33 356/450 |
| 2011/0261164 | A1* | 10/2011 | Olesen | G01N 15/1475 348/46 |
| 2011/0311978 | A1* | 12/2011 | Makarewicz, Jr. | B01F 3/0807 435/6.12 |
| 2012/0200671 | A1* | 8/2012 | Silveira | G02B 27/0025 348/46 |

OTHER PUBLICATIONS

Zheng, et al., "Sub-Pixel Resolving Optofluidic Microscope for On-Chip Cell Imaging," Lab on a Chip, vol. 10, 3125-3129, (2010).
Sharpe, et al., "Optical Projection Tomography as a Tool for 3D Microscopy and Gene Expression Studies," Science, vol. 296, pp. 541-545, (2002).
Bishara, et al., "Holographic Opto-Fluidic Microscopy," Optics Express, vol. 18, No. 26, pp. 27499-27510, (2010).
Molder, et al., "Non-Invasive, Label-Free Cell Counting and Quantitative Analysis of Adherent Cells using Digital Holography," Journal of Microscopy, vol. 232, (2008).
Golibersuch, "Observation of Aspherical Particle Rotation in Poiseuille Flow via the Resistance Pulse Technique," Biophysical Journal, vol. 13, pp. 265-280 (1973).
Lee, et al., "The Application of On-Chip Optofluidic Microscopy for Imaging Giardia Lambliai Trophozoites and Cysts," Biomedical Microdevices, vol. 11, pp. 951-958 (2009).
Murphy, Fundamentals of Light Microscopy and Electronic Imaging; Wiley & Sons, Inc, US, (2001).
Teague, "Deterministic Phase Retrieval: a Green's Function Solution," Journal of Optical Society of America, vol. 73, No. 11, pp. 1434-1441, (1983).
Streibl, "Phase Imaging by the Transport Equation of Intensity," Optics Communications, vol. 49, No. 1, (1984).
Marchand, et al., "Optischen Abbildung unter Uberschreitung der Beugungsbedingten Auflosungsgrenze," Optics Acta: International Journal of Optice, vol. 10, No. 3, pp. 241-255 (1963), English Translation of Abstract Only.
Neil, et al., "Method of Obtaining Optical Sectioning by Using Structured Light in a Conventional Microscope," Optics Letters, vol. 22, No. 24, pp. 1905-1907 (1997).

* cited by examiner

FLUID CHANNELS FOR COMPUTATIONAL IMAGING IN OPTOFLUIDIC MICROSCOPES

CROSS-REFERENCE TO PRIOR FILED APPLICATIONS

This application claims priority to U.S. provisional application 61/699,020 which was filed on Sep. 10, 2012 and U.S. provisional application 61/699,003 which was filed on Sep. 10, 2012 both of which are incorporated herein in their entirety.

TECHNICAL FIELD

This invention relates generally to optofluidic microscopes (OFM) and modifications to OFMs.

BACKGROUND

Optofluidic microscopes allow imaging of small objects, typically cells, that travel through a fluid channel. There are two types of optofluidic microscopes: those that image only intensity and those that use interference (holography) to record both intensity and phase. The former method is the simplest but lacks key information, while the latter requires additional beams and optical paths. To date, both methods measure only a 2D surface and are limited to imaging structures whose size is larger than a wavelength. Improvements in optofluidic microscope systems would be desirable

SUMMARY OF THE INVENTION

A microscope is disclosed, the microscope having a light source defining an optical axis along a Z direction and a detector disposed in X-Y direction, orthogonal to the optical axis, the detector configured to capture images of an object. The microscope includes a fluid channel having an inlet and an outlet configured with a fluid flow to transport the object from the inlet to the outlet. The detector is configured to capture a plurality of images of the object as the object moves from the inlet to the outlet. The plurality of images of the object have different heights of the sample with respect to the detector as the sample flows through the channel.

The light source may be sunlight, an electric light source and/or a fluorescent light source. A pinhole or slit aperture may be introduced to control a range of illumination or detection angles. A pinhole or slit aperture may be introduced to allow point-by-point or line-by-line, scanning by the flow. The channel may be tilted with respect to the optical axis. The detector may be tilted with respect to the optical axis.

A lens may be placed in the optical path. The lens may be tilted with respect to the optical axis. The microscope has an imaging condition and the lens, object and detector has a spacing that satisfies the imaging condition. A first distance between the object and the lens and second distance between the lens and the detector may be the same.

The microscope may include an objective lens disposed along the optical axis wherein the fluid channel is configured to position the object in a focal plane of the objective lens when the object is located on the optical axis. The microscope may include a processor configured to generate a three dimensional image of the object using the plurality of images of the object. The detector may have a frame rate and the fluid channel may have a flow rate that are selected to provide a plurality of images that are shifted via a sub-pixel displacement distance.

The fluid channel may have a constant flow rate. The microscope may include a processor configured to measure, quantify, and correct for non-constant flow rate. The fluid channel may be configured to induce rotation of the object as it moves from the inlet to the outlet. The fluid channel may be configured to fix an orientation of the object as it moves from the inlet to the outlet. Two or more images may be used to obtain a phase of the object. Two or more images may be used to obtain a surface profile of the object. Two or more images may be used to acquire a focal stack of the object. Two or more images may be used to obtain an internal volume structure of the object. Two or more images may be used to obtain different angular views of the object. A structured light pattern may be used to illuminate the object. The structured light pattern may be periodic. The structured light pattern may have a chirped period or multi-scale spacing. Sample displacements from the flow may be used to remove phase ambiguity from structured illumination. A diffraction grating may be configured for structured illumination.

Another microscope is disclosed. The microscope has a light source defining an optical axis along a Z direction and a detector disposed in X-Y direction, orthogonal to the optical axis, the detector being configured to capture images of an object. The microscope includes a fluid channel having an inlet and an outlet configured with a fluid flow to transport the object from the inlet to the outlet. The detector is configured to capture a plurality of images of the object as the object moves from the inlet to the outlet. A structure is disposed in the optical path to pattern the light so that the detector records a product of the light pattern and the object features. The structure in the optical path to pattern the light may be a diffraction grating. The structure in the optical path to pattern the light may be an amplitude mark or phase mask. The structured light pattern may be generated by a pair of interfering light sources. The structured light pattern may be periodic. The structured light pattern may have a chirped period or multi-scale spacing. Sample displacements from the flow may be used to remove phase ambiguity from structured illumination.

DETAILED DESCRIPTION

The disclosed modifications relate to imaging in optofluidic microscopes (OFM) using a fluid channel. A typical OFM includes three basic parts: an illumination source, a fluid system, and an image detector. The illumination system may use a variety of sources such as sunlight, lasers and LEDs. The detector is typically a CCD sensor although other sensors may be used. The fluid system includes a channel that is etched into a transparent substrate, such as PDMS, which may be bonded directly to the CCD. Input and output ports are then added to the channel to ensure a fluid flow across it.

Figure 1A:
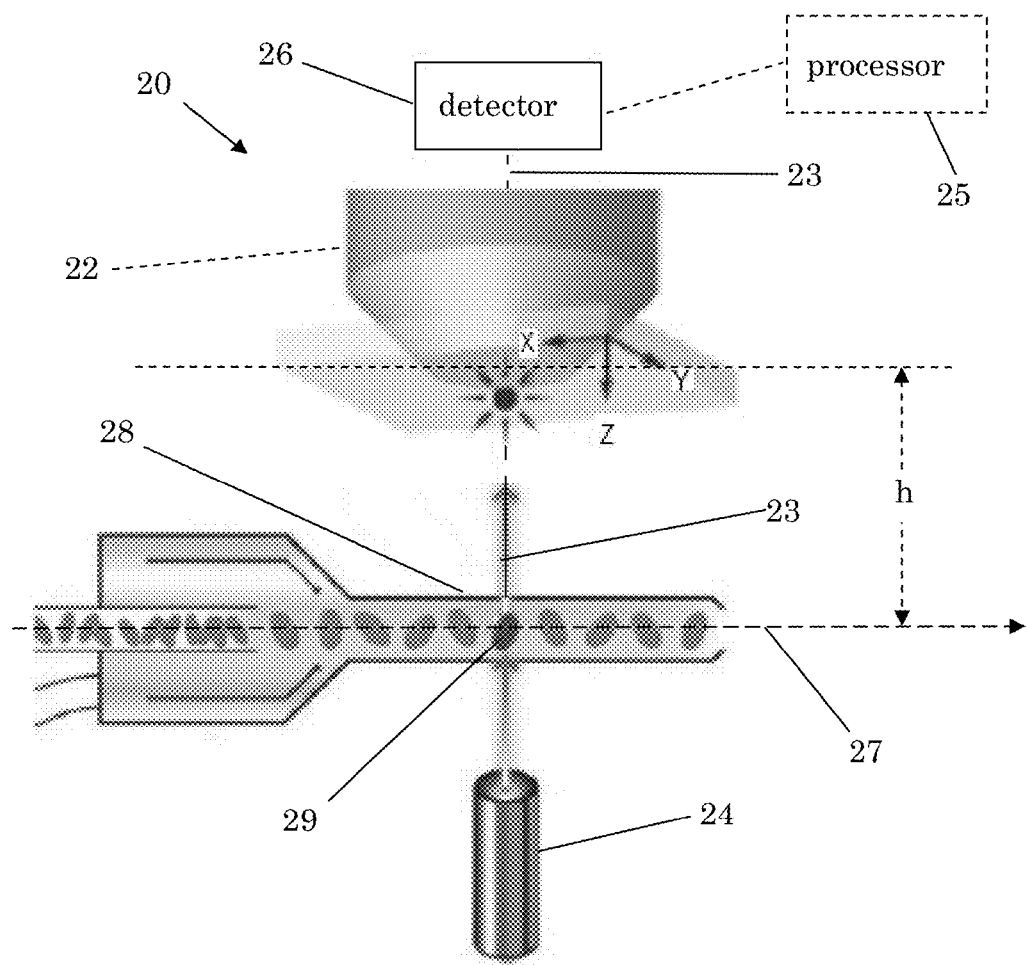
FIG. 1a is a schematic block diagram of an optofluidic microscope (OFM)

FIG. 1a shows a schematic block diagram of an OFM 20. It should be understood that such microscopes may include additional features that are not shown such as a stage, revolving nosepiece with multiple objective lenses, condenser lens, iris, coarse and fine focus and the like. Such aspects are well known in the art. The OFM 20 includes a light source 24 and a detector 26. The OFM 20 may optionally include an objective lens 22. The objective lens 22 includes an optical axis as generally shown by reference number 23. In configurations without an objective lens, the light source light source typically defines the optical axis along a Z direction and the detector 26 is disposed in X-Y direction.

Detector 26 may be any type of suitable imaging detector such as a CCD and may be coupled to a processor 25. The OFM 20 also includes a fluid channel 28 configured to flow one or more objects (specimens) 29 along a flow path 27 through the fluid channel 28 for imaging by the detector 26. In this example, the flow path 27 through the fluid channel 28 is oriented generally orthogonal to the optical axis 23. That is, the flow path is configured to minimize height changes (e.g., in the Z direction) in the objects 29 with respect to the objective lens 22 as the objects 29 move through the fluid channel 28. In this example, the height (h) between the object and the objective lens or detector is essentially constant. It should be understood that the objective lens or detector may be movable in the X, Y and Z directions with respect to fluid channel 28 for imaging as is well known in the art. For example, the objective lens may be moved in the Z direction to set adjust the focus (e.g., to set the focal depth or focal plane). Similarly, the objective lens may be moved in the X-Y location to position the lens in a desired location with respect to the fluid channel 28.

Figure 1B:
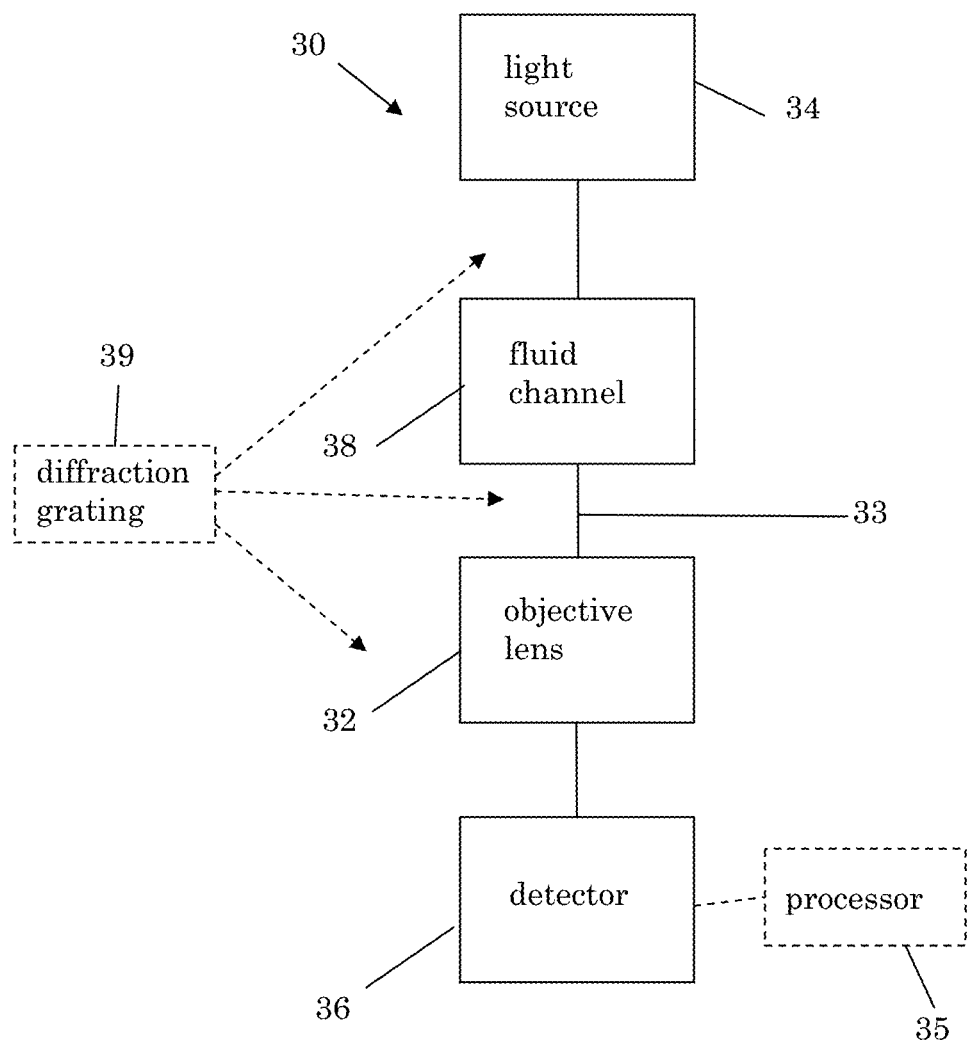
FIG. 1b shows a block diagram of an OFM including an objective lens, a light source and a detector.

It should be understood that a variety of configurations are possible without departing from the scope of this disclosure. For example, FIG. 1b shows an OFM 30 including an objective lens 32, a light source 34 and a detector 36. The objective lens 32 includes an optical axis as generally shown by reference number 33 as discussed above. In this example, the fluid channel 38 is placed over the imaging sensor (detector) 26 and objects (such as cells) are flowed through the channel 38. A light source 34 is disposed above the fluid channel 38 to create an image of the objects on the sensor 26 below. The detector 36 may be coupled to a processor 35 as discussed above. A diffraction grating may also be inserted into the optical path as shown generally by reference number 39.

Figure 2A:
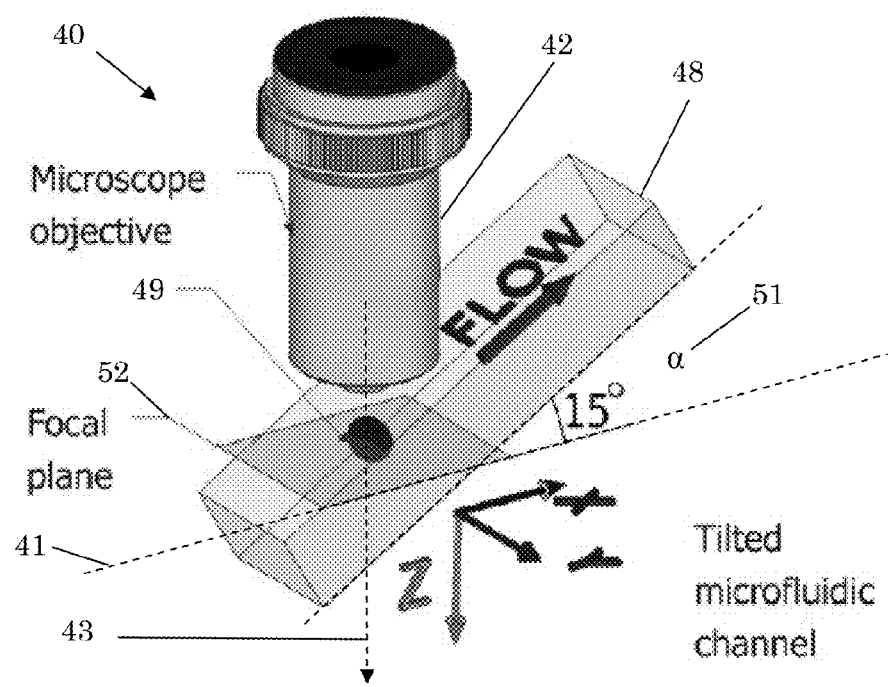
FIG. 2a shows an OFM including an objective lens and a tilted channel.
Figure 2B:
FIG. 2b shows samples as they flow along the channel axis and pass across the focal plane.

FIG. 2a shows an OFM 40 including an objective lens 42. The light source and detector are not shown in order to simplify the drawing. A tilted fluid channel 48 (e.g., in the Z direction) is disposed at an angle α (shown generally by reference number 51) that is displaced from the traditional orthogonal plane (shown generally by reference number 41). In general, the fluid channel 48 is disposed so as to induce height changes in the object 49 with respect to the objective lens 42 as the object 49 moves through the fluid channel 48. In this example, the objective lens is configured to establish a focal plane 52 so that at least a portion of the object 48 is in focus as the object passes through the optical axis 43 of the objective lens 42. In operation, the tilted channel creates multiple heights between the object 49 and the objective lens 42 or sensor. In one embodiment, the object 49 flows into the channel at a constant velocity. Multiple images of the object 49 are recorded by a camera operating at a constant frame rate. Additional objects may also be observed as they flow along the channel axis and pass across the focal plane. FIG. 2b shows samples as they flow along the channel axis 53 and pass across the focal plane 52.

The structure disclosed herein allows the numerical reconstruction of phase from two different images taken at different locations along the flow path of the channel (at different heights) and enables full 3D profiling using the technique of optical cross-sectioning. The technique is applicable to any size feature, including sub-wavelength features below the classical diffraction limit. This structure allows for leveraging of existing microscopes and imaging algorithms, including phase retrieval through defocus, e.g. by transport of intensity equations, and superresolution imaging via sub-pixel shifting and structured illumination.

In an experimental setup as generally shown in FIG. 2a, a 500-μm-wide, 50-μm-deep microfluidic channel is etched on a glass slide and located at the focal plane of a standard wide-field microscope. The slide is tilted at a 15-deg angle, α, with respect to the optical axis of the microscope objective, chosen to represent a good compromise between magnification and axial defocusing. The channel is illuminated with incoherent white light, and a 25× magnified image is recorded by a video camera operating at a constant frame rate of 30 frames/s. As a test case, a suspension of 15 μm yeast cells in glycerol is flowed through the microfluidic channel.

The frame rate and flow speed are adjusted so that each sample will be recorded in 100 consecutive frames as it passes from one end of the window of observation to the other. A constant flow is maintained using a fixed pressure difference (a 50-cm hydrostatic water column) between the channel input and output, and the exposure time is adjusted to reduce the flow induced blur below the resolution limit of the imaging system. Narrow channel depth and high fluid viscosity guarantee a Hagen-Poiseuille type laminar flow. In addition, the concentration of particles is lower than 250 $\mu L^{-1}$ for easy separation and to reduce interactions between flowing particles.

The parabolic velocity flow ensures that particles flow at a constant velocity (v) along the channel axis but experience a shear-induced rotation at other points. As the acquisition of accurate focal stacks relies on the absence of rotation (or its compensation), the setup has been designed to minimize the effects of shear in all directions. Along the channel axis u, the absence of shear, $\nabla v \cdot u = 0$, is a property of the laminar flow. Along the y axis, shear-induced rotation effects are minimized by observing samples flowing in the middle part of a wide channel. Similarly, along the z axis, rotating objects are excluded by considering only particles flowing at the highest velocity in the middle of the channel, where the shear effects cancel. In other embodiments, object rotation may be deliberately induced, e.g., to provide for multiple viewpoints. This can be achieved e.g., by changing the injection point or imaging different parts of the flow.

Figure 3A:
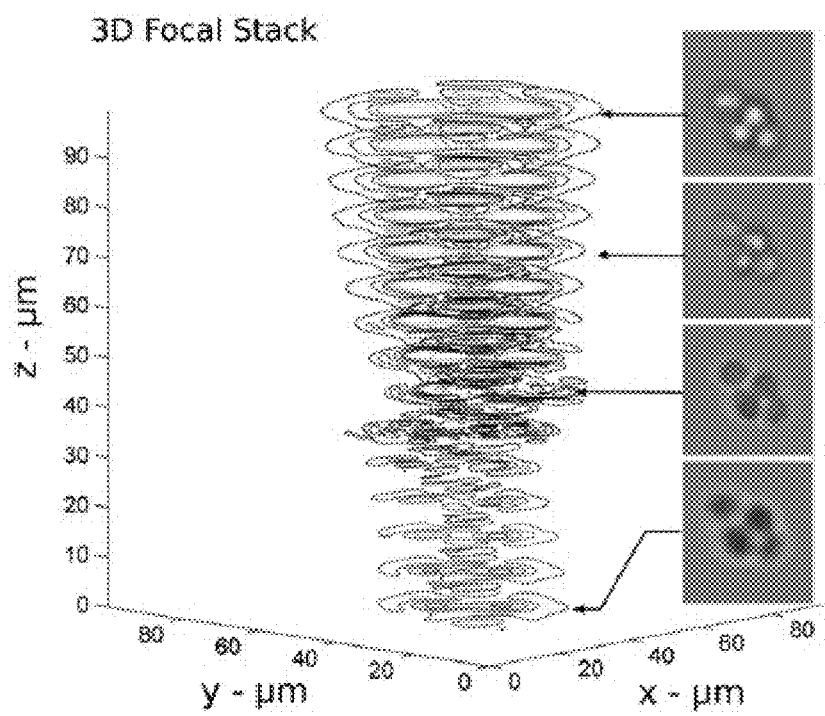
FIG. 3a shows focal stacks that are generated by observing samples as they flow in the tilted microfluidic channel.
Figure 3B:
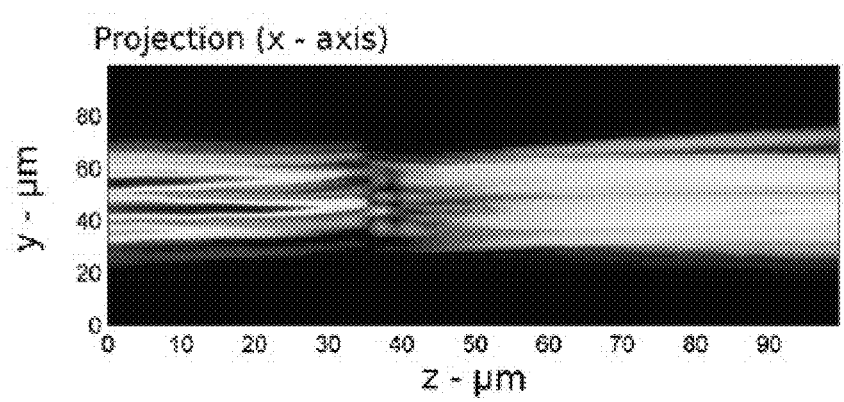
FIG. 3b shows a normalized intensity of focal stack with background subtracted.

Focal stacks are generated by tracking samples flowing into the channel, as shown in FIG. 3a. It should be understood that focal stack data is stored in a memory, e.g., connected to processor 25, 35. Constant flow velocity and frame rate enable the accumulation of ≈100 frames progressively defocused along the z axis. An object-tracking algorithm based on defocusing invariant properties of the center of gravity of the image is used for better accuracy. FIG. 3a generally shows the measured iso-intensity contours of yeast cells through focus (≈36 μm). Insets show direct images of cells. FIG. 3b shows a normalized intensity of focal stack with background subtracted.

Figure 4A:
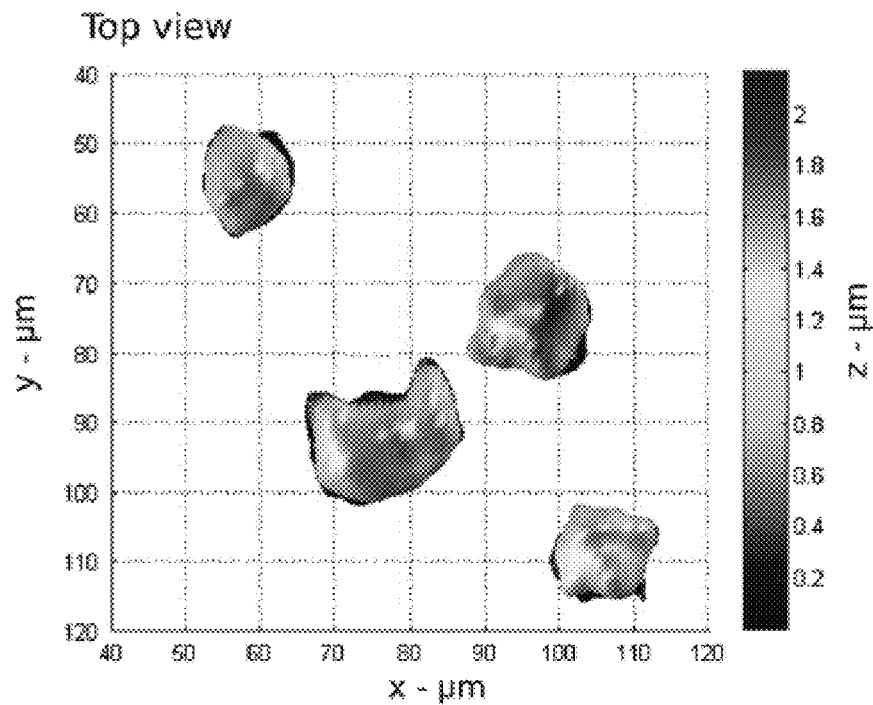
FIG. 4a shows a three-dimensional (3-D) structure reconstructed from flowing yeast cells, an iso-level surface shows subcellular structures at the surface of the cellular membrane.

Focal stack data may be further processed to construct a 3 dimensional image. FIG. 4a shows a three-dimensional (3-D) structure reconstructed from flowing yeast cells, an iso-level surface shows subcellular structures at the surface of the cellular membrane. The focal stack, S, and the point spread function, P, are each processed using the techniques disclosed in Nicolas C. Pégard and Jason W. Fleischer, *Three-dimensional deconvolution microfluidic microscopy using a tilted channel*, Journal of Biomedical Optics, April 2013, Vol. 18(4), pp. 040503-1-040503-3 which is incorporated herein in its entirety. 3-D data is retrieved, enabling the construction of iso-level surface contours. FIG. 4(a) shows a projection of these contours along the optical axis, revealing small-scale surface features (≈1-2 μm) which are clearly resolved (though smoothed somewhat by the regularization process). Most likely, they are due to early-stage budding, though many other factors can contribute to their morphology.

Figure 4B:
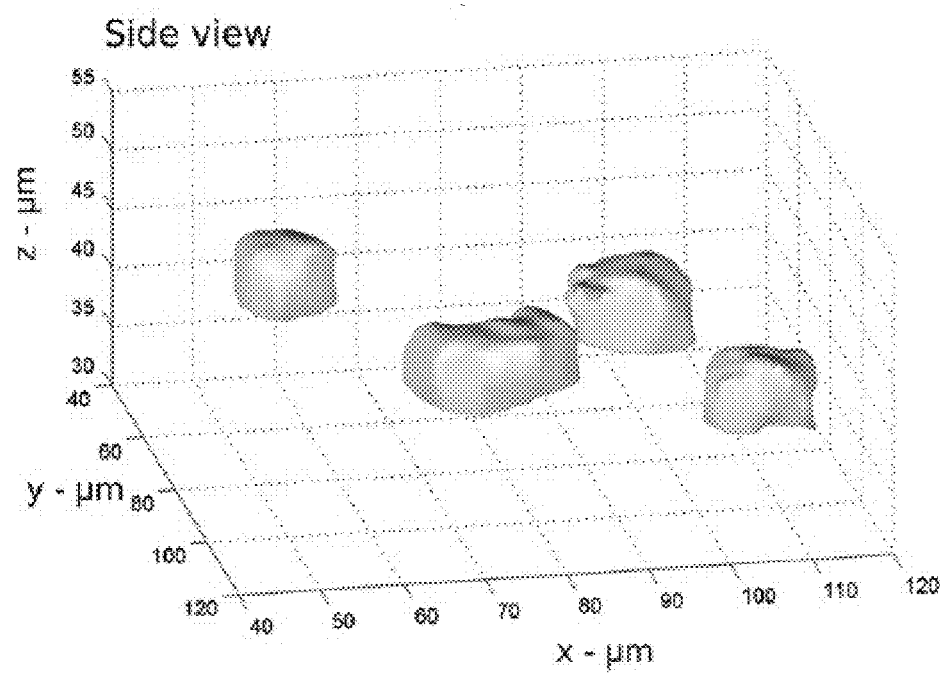
FIG. 4b shows a three-dimensional (3-D) structure reconstructed from flowing yeast cells with a three-quarter view of the samples, showing smooth structure of the cell walls and relative height in the channel

FIG. 4b shows a three-dimensional (3-D) structure reconstructed from flowing yeast cells with a three-quarter view of the samples, showing smooth structure of the cell walls and relative height in the channel. FIG. 4(b) gives contours from the side, showing that all the cells lie in the same vertical plane (a result of the controlled injection) and that each cell has flat side walls. Such deformation is common in flowing cells 21 and is often used as a diagnostic. As stated above, both the observed shapes and surface profiles are minimally affected by noise in the deconvolution process, as Wiener regularization optimally smooths the reconstructed profiles. Many of the details that are hidden in standard imaging using 2-D projections, such as cell orientation, 3-D shape, and surface roughness, are readily apparent in the volume images here.

In another embodiment, the channel may be modified to induce a rotating flow for 3-D optofluidic tomography. To date, there are two methods to obtain three-dimensional data about an object: holography and tomography. The former involves interference with a reference beam while the latter requires multiple illumination from various angles. Only holography been applied to optofluidic microscopes, though at the expense of sensitivity. The disclosed approach emphasizes simplicity and high throughput of regular OFMs, by rotating the object during flow, which enables full 3D reconstruction of the object.

The current method of optical projection tomography for cells, e.g. used by Vision Gate Inc., is the encasement of the cell in a capillary tube. This is an individual cell method that does not allow for high throughput, as an optofluidic device would. Cell function and classification is often determined by its structure. Common examples include protein structure for "lock-and-key" recognition and different morphology for pathology, such as anemic and cancerous cells. Disclosed herein is an approach that uses rotating flow within the optofluidic channel. Since the object rotates and not the light source, full 3D reconstruction can be obtained with only a single, fixed illumination source. This enables easy implementation to existing optofluidic microscope designs and greatly simplifies the setup.

As disclosed above, the fluid system includes a channel that is etched into a transparent substrate, such as PDMS, which may be bonded directly to the detector. Input and output ports are then added to the channel to ensure a fluid flow across it. In order to induce a rotation flow, the object may be injected near the wall of the channel, so that it experiences a velocity shear. The object will then rotate as it translates along the channel.

In another embodiment, the fluid channel is rifled, so that the fluid rotates as it flows. In turn, any object within the fluid, such as a cell, will rotate about its axis of propagation. For a fixed illumination source, different projections through the object will recorded on the sensor; these are then numerically combined into a full 3D reconstruction. Other methods of rotating the flow are possible, such as vanes or pumps on the input and/or output ports, but such approaches may be less practical because of the relatively viscous Stokes flow involved.

Figure 5:
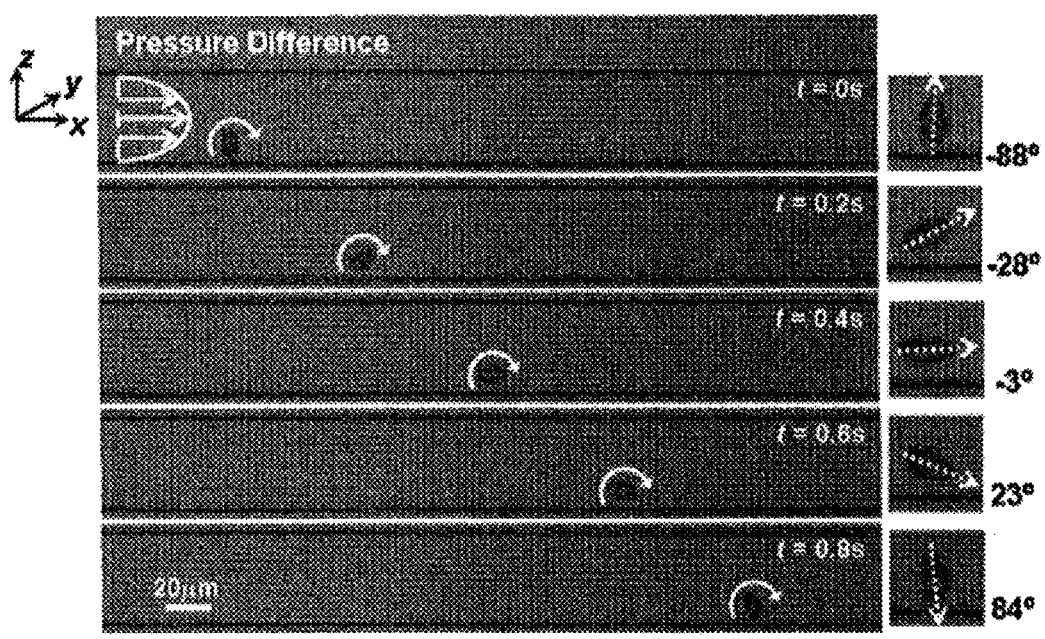
FIG. 5 shows experimental observation of Giardia cyst rotation in channel flow.

In addition to the typical OFM limitations of throughput and optical resolution, there is the added complication of variable object height and rotation rate. Also, rifling the channel will introduce structure (refractive index modulations) in the optical path. However, this structure is fixed and can be measured for later removal (deconvolution) numerically. FIG. 5 shows experimental observation of Giardia cyst rotation in channel flow. Prior systems are configured to minimize this motion, using such methods as electrokinetics to counteract the shear. Here, we use the rotation for multiple views and 3D tomographic reconstruction. Additional disclosure pertaining to the construction of 2D and 3D images from optofluidic microscopes is contained in PCT/US2011/029542 which is incorporated herein in its entirety.

The resolution of an optical imaging system is subject to the diffraction limit, which for a fixed wavelength is governed by the numerical aperture (NA) of the system. One technique to go beyond this limit is structured illumination (SI), in which a known illumination pattern (usually periodic) is projected onto a sample. Spectral beating of this pattern with the object modes folds high resolution information into lower spatial frequencies (Moiré patterns), which can be detected by the imaging device. Deconvolving the photonic aliasing can improve resolution by a factor of two in the linear case, with greater improvements possible using nonlinearity. This imaging technique, however, requires the acquisition of several raw images (at least three) with a series of precise displacements of the illumination pattern in order to remove phase ambiguity. Previous SI systems relied on mechanical moving parts (e.g., piezoelectric actuators) or on a spatial light modulator (SLM) to perform the shift. These methods add complexity to the imaging system and can significantly reduce the image acquisition speed. Further, mechanical movement is subject to vibration error and artifacts, while SLMs are limited by their pixel size.

Separate from the SI approach, fluidic imaging systems for improved resolution have been developed. Typically considered in microfluidic microscopes and aquatic imagers, these systems have received renewed attention with the development of integrated optofluidic devices, which are lensless imagers that place flowing samples directly over a detector. Among their advantages are simple and low cost object manipulation, with little or no sample preparation. In most devices, the flow is used only to provide object throughput. However, as disclosed herein, flow can be used as an additional degree of freedom for imaging. As discussed above, the fluid transport may be used as a scanning mechanism to enhance resolution, e.g., by taking multiple frames with sub-pixel displacements. Using this approach, resolution is limited by the camera frame rate (vs. flow speed) and edge effects from pixels. Typically illumination is kept as uniform as possible.

Using the techniques disclosed herein it is possible to we add the element of structured illumination to fluidic imaging. Unlike previous setups combining flow and patterned illumination, which used the flow only for throughput (e.g., to measure gas kinetics, live cells or two-phase flow), it is possible to use a fixed illumination pattern and let the flow itself provide the necessary scanning. This eliminates the need for pattern shifting and the high flash speeds needed to freeze motion. From a flow perspective, the instant wavenumber (k-space) shift gives improved spatial resolution at greater speeds than sub-pixel methods, with better use of camera dynamic range. The combined scheme thus retains all the benefits of fluidics, including high sample throughput and object sorting, while enabling easy integration with existing flow and imaging systems.

Figure 6:
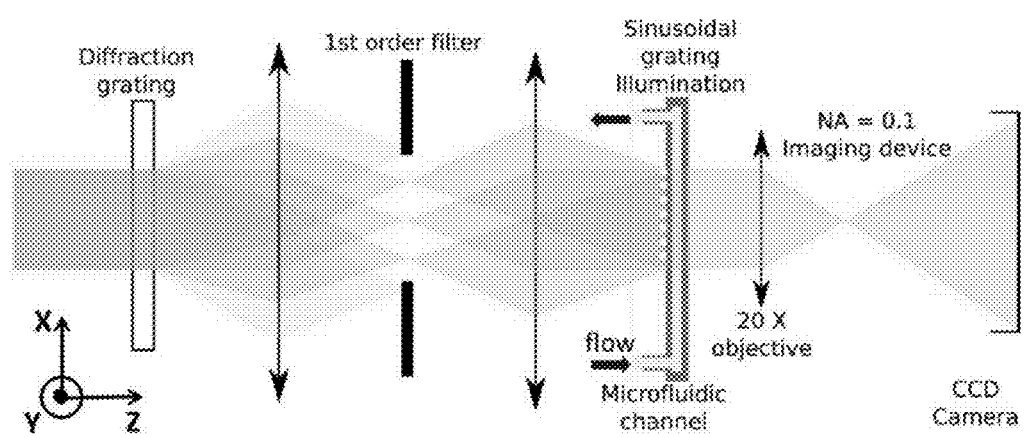
FIG. 6 is a block diagram of an OFM configured with structured illumination.

FIG. 6 is a block diagram of an OFM configured with structured illumination. A 500 μm wide, 50 μm deep fluidic channel is at the focal plane of a 20× objective lens. The imaging system has low numerical aperture (NA=0.1). The structured illumination source is a steady sinusoidal profile (2:78 μm stripes) orthogonal to the flow direction. Images are recorded on a CCD camera at a frame rate 15 fps.

To generate the structured light, a 532 nm continuous laser is patterned using a transmission grating and then demagnified to reduce fringe spacing. This light then illuminates the channel with a steady sinusoidal pattern: 2:78 μm stripes orientated orthogonal to the fluid flow direction. While the SI technique will work for any imaging system, including lensless ones, in this example the channel is placed at the focal plane of an optical microscope. As a compromise between magnification and field of view, e.g., for water analysis, a 20× optical objective is used. The objective is part of a 4f imaging configuration with an aperture located at the confocal plane. The resulting value of the numerical aperture (NA=0.1) corresponds to a resolution limit of approximately 4 μm.

A suspension of yeast particles in glycerol is flowed through the microfluidic channel at a constant flow velocity. Multiple images are recorded by a charge-coupled device (CCD) camera (pixel size 9:9 lm) at a constant frame rate (15 fps). FIGS. 2(a)-2(c) show three consecutive frames. It is clear that different features of the object are revealed as it flows past the stationary illumination pattern. Additional details relating to numerical reconstruction using data generated from an OFM using SI are disclosed in Chien-Hung Lu, Nicolas C. Pégard and Jason W. Fleischer, *Flow-based structured illumination*, Appl. Phys. Lett. 102, 161115 (2013) which is incorporated herein in its entirety.

In another embodiment, a microfluidic channel is illuminated with an LED through a slit aperture (along the y axis) which restricts the light field to a fan of light expanding in the vicinity of the channel flow axis. A cylindrical lens (f=2 mm) is located at a focal distance from the slit aperture. Such a configuration enables the acquisition of multiple projections of the slit aperture image for a continuous range of perspective angles limited by the numerical aperture of the microscope objective.

Figure 7:
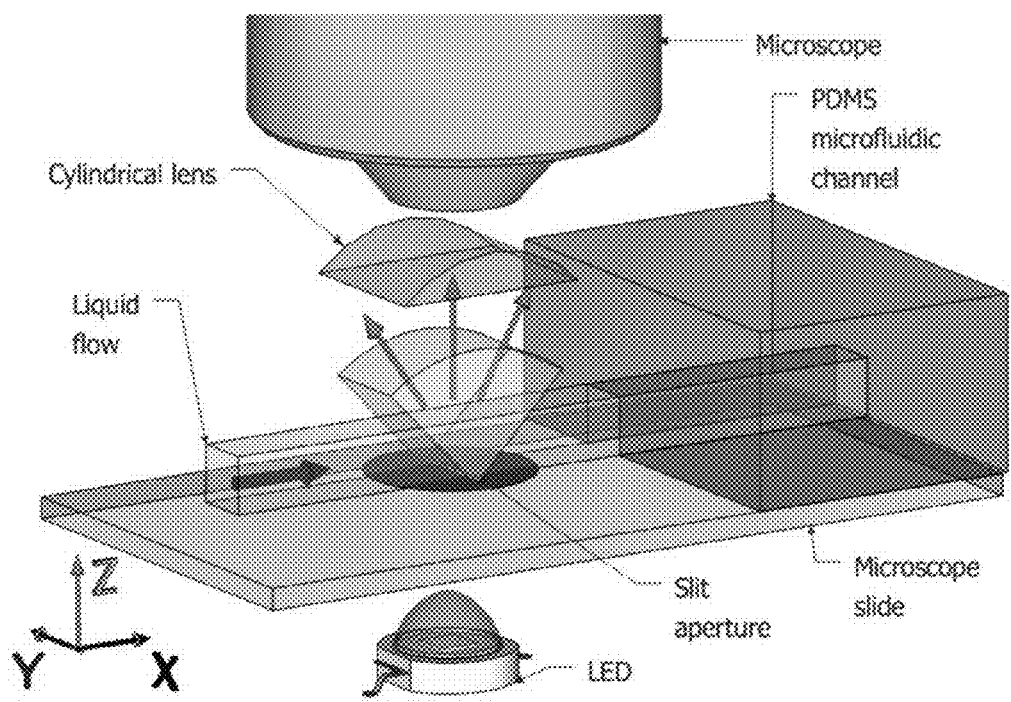
FIG. 7 is a block diagram of an OFM configured with flow-scanning optical projection tomography.

FIG. 7 is a block diagram of an OFM configured with flow-scanning optical projection tomography. A 100 μm wide, 100 μm deep fluidic channel is at the focal plane of a 100× objective lens. A slit aperture creates a fan of light and the transmitted light field is observed in phase-space with a Fourier lens. The imaging system has high numerical aperture (NA=0.7). Images are recorded in the phase-space domain on a CMOS camera at a frame rate 100 fps. Each frame contains multiple views of the slit image for a wide range of observation angles.

As the sample flows at constant speed into the channel, multiples frames are recorded at frame rate adjusted so that the sample displacement between consecutive frames satisfies δx≈2 μm.

Tomographic data is acquired line-by-line as the sample flows into the channel, and a 3D image is retrieved using a tomography reconstruction algorithm, here an Inverse Radon transform.

Figure 8:
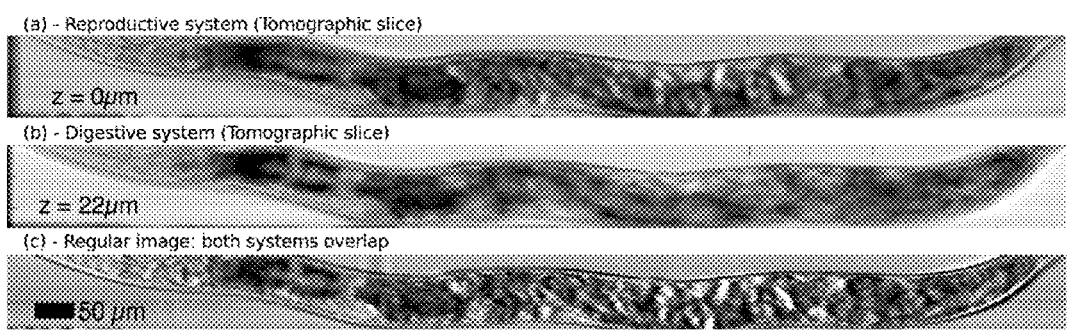
FIG. 8 shows experimental results on live, freely swimming C. elegans.

FIG. 8 shows experimental results on live, freely swimming *C. elegans*. Two tomographic slices at different depth levels show separated views and precise xyz location of the reproductive system with eggs (*a*), and of the digestive system and the intestine (*b*). In a regular white light microscopy image (*c*), these internal features overlap and are harder to detect or locate.

The references listed herein are also part of the application and are incorporated by reference in their entirety as if fully set forth herein. It should be understood that many variations are possible based on the disclosure herein. Although features and elements are described above in particular combinations, each feature or element can be used alone without the other features and elements or in various combinations with or without other features and elements. The methods or flow charts provided herein may be at least partially implemented in a computer program, software, or firmware incorporated in a non-transitory computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs)

What is claimed is:

1. A microscope comprising:
   a light source defining an optical axis vertically along a Z direction;
   a fluid channel having an inlet and an outlet configured with a fluid flow to transport an object from the inlet to the outlet, wherein the fluid channel is tilted vertically with respect to the optical axis;
   a characterized three-dimensional (3D) point-spread function; and
   a detector disposed in an X-Y direction, orthogonal to the optical axis, wherein the detector is configured to capture a plurality of images of the object as the object moves from the inlet to the outlet, and the plurality of images of the object are recorded at different heights of the object relative to the detector as the object moves from the inlet to the outlet to enable 3D profiling of the object.

2. The microscope of claim 1 wherein the fluid channel has a constant flow rate.

3. The microscope of claim 1 wherein the fluid channel is configured to induce substantial rotation of the object as it moves from the inlet to the outlet.

4. The microscope of claim 3 wherein the fluid channel is rifled.

5. The microscope of claim 3 wherein the object is injected near a wall of the fluid channel.

6. The microscope of claim 1 wherein the fluid channel is configured to minimize rotation of the object as it moves from the inlet to the outlet.

7. The microscope of claim 6 wherein the object is observed near the center of the fluid channel.

8. The microscope of claim 1 wherein the 3D point-spread function is calibrated by imaging an object at different heights along the optical axis.

9. The microscope of claim 8 wherein the object used for calibration is a bead.

10. A microscope comprising:
  a light source defining an optical axis vertically along a Z direction;
  a fluid channel having an inlet and an outlet configured with a fluid flow to transport an object from the inlet to outlet, wherein the fluid channel is tilted vertically with respect to the optical axis;
  a slit aperture between the light source and the fluid channel to illuminate the fluid channel, the slit aperture to control the spatial distribution, spatial coherence, and angular spectrum of the light source;
  a characterized three-dimensional (3D) point-spread function; and
  a detector disposed in an X-Y direction, orthogonal to the optical axis, wherein the detector is configured to capture a plurality of images of the object as the object moves from the inlet to the outlet, the plurality of images of the object being recorded at different heights of the object relative to the detector as the object moves from the inlet to the outlet to enable 3D profiling of the object.

11. The microscope of claim 10 wherein the fluid channel has a constant flow rate.

12. The microscope of claim 10 wherein the fluid channel is configured to induce substantial rotation of the object as it moves from the inlet to the outlet.

13. The microscope of claim 12 wherein the fluid channel is rifled.

14. The microscope of claim 12 wherein the object is injected near a wall of the fluid channel.

15. The microscope of claim 10 wherein the fluid channel is configured to minimize rotation of the object as it moves from the inlet to the outlet.

16. The microscope of claim 15 wherein the object is observed near the center of the fluid channel.

17. The microscope of claim 10 wherein a cylindrical lens is used to collect the light and project it onto the detector.

18. The microscope of claim 17 wherein the lens is placed to satisfy a Fourier condition for the object.

19. The microscope of claim 17 wherein the lens is placed to provide a fractional Fourier transform of the object.

20. The microscope of claim 10 wherein a plurality of images is used to form a tomographic reconstruction of the object.

21. The microscope of claim 10 wherein a plurality of images is used to reconstruct a phase of the object.

* * * * *